March 25, 1947. G. DE RUITER Plant Pat. 726
ROSE PLANT
Filed Dec. 8, 1942
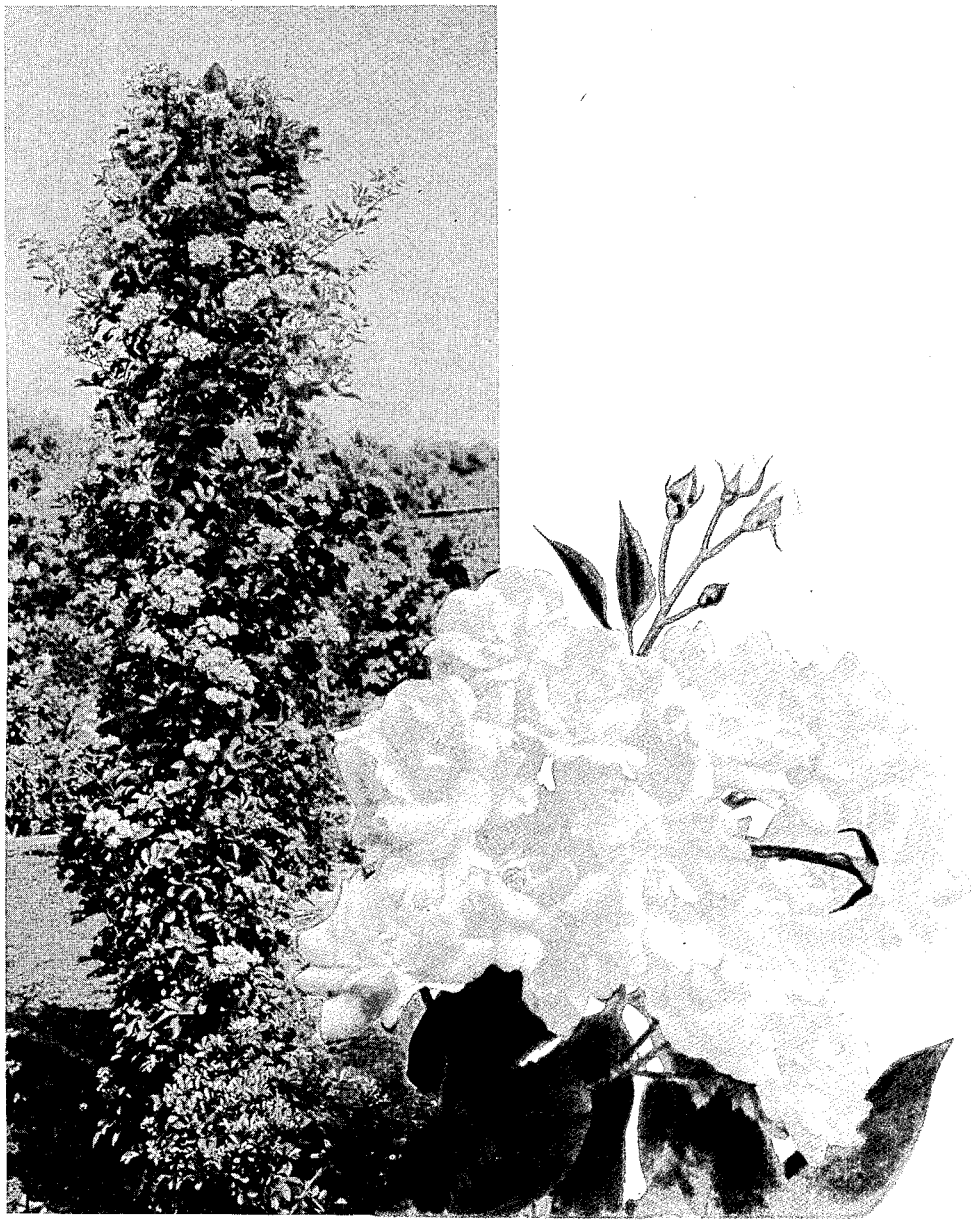
Inventor
G. De Ruiter
By Robert Robb
Attorneys Patented Mar. 25, 1947

Plant Pat. 726

UNITED STATES PATENT OFFICE

726

ROSE PLANT

Gerrit de Ruiter, Hazerswoude, Netherlands, assignor to Jackson & Perkins Company, Newark, N. Y., a corporation of New York Application December 8, 1942, Serial No. 468,293

1 Claim. (Cl. 47—61)

The present discovery relates to a new and distinct variety of rose plant, originating as a sport of an unnamed orange colored polyantha seedling.

This new variety is characterized as to novelty primarily by its climbing habit of growth, as distinguished from the dwarf habit or bush form of growth of its parent.

More particularly, however, it is the form and coloring of the blossoms of this plant and the persistence of the coloring which marks its claim to distinctiveness with relation to those varieties of the same general color class as its parent. That is to say, the particular tone of scarlet coloring, i. e., scarlet red, is given a contrastiveness by the whitish appearance of the eye which seems to lighten up the whole of the surrounding area when the blossoms are observed from the standpoint of general tonality. This is shown as nearly as possible in the colored portion of the illustration in the accompanying drawing, and it is notable also in connection with the appearance of these blossoms that there is an unusual absence of blue or purple shadings so commonly found in roses of this general color.

The nearest approach to the present variety is found to be the known "Princess van Orange" (Pl. Patent #106) insofar as concerns the color character, but the new rose differs from this known variety in many respects as will be clearly apparent from the detailed description of the new rose when compared with the characteristics of "Princess van Orange." It is especially noted that the shape and number of petals of the blossom of the new rose differ widely from the variety above mentioned, and the fact that the new variety grows to greater height, as well illustrated in the accompanying drawing, produces longer breaks, and retains the bright clear coloring at all times, said new variety is definitely distinguishable from "Princess van Orange."

Furthermore, the new rose, by comparable tests, is found to be hardier than "Priness van Orange," and more useful for pot forcing than the latter, to say nothing of the usual uses for pergolas, trellises, and fences.

Asexual reproduction of this new variety shows the foregoing characteristics come true to form and are established.

The following is a detailed description of the new variety, all color terminology being in accord with Ridgway's Color Standard:

Parentage: Sport. Parent variety—climbing sport of unnamed orange colored polyantha seedling.

Classification: Botanic and commercial—climbing rose of polyantha.

*Flower*

(Observations made in the gardens of Jackson & Perkins Company, Newark, New York, in June, 1942.)

Blooming habit: Blooms once—early; has a tendency to give few blooms in the fall.

Bud:

*Size.*—Small.

*Form.*—Short with flat top; is not affected by wet or hot weather.

*Color.*—When sepals first divide—Nopal Red, Plate 1; when petals begin to unfurl—Scarlet Red, Plate 1; when half blown—inside of petals, Scarlet Red, Plate 1, and Scarlet, Plate 1; reverse of petals, between Scarlet Red, Plate 1, and Rose Doree, Plate 1.

*Sepals.*—Branched; curl back when petals begin to unfurl. *Color*—inside—Light Lumiere Green, Plate 17; outside—Deep Chrysolite Green, Plate 31.

*Calyx.*—Shape—apple. Size—small. Aspect—smooth. Color—Deep Chrysolite Green, Plate 31. Odor when rubbed—none.

*Peduncle.*—Length—short. Aspect—prickly. Color — Absinthe Green, Plate 31. Strength—erect; slender.

*Opening.*—Bud opens well; is not affected by adverse conditions.

Bloom:

*Size.*—Small. Average size when fully expended, 1½".

*Borne.*—In clusters, rounded.

*Stems.*—Medium length; strong.

*Form.*—When first open, cupped. Permanence—retains its form to the end.

*Petalage.*—Semi-single (two rows of petals). Number of petals under normal conditions, 15.

*Color.*—Center of flower—between Scarlet Red, Plate 1, and Scarlet, Plate 1. Outer petals—between Scarlet Red, Plate 1, and Scarlet, Plate 1. Base of petals (aiglet)—White, Plate 53, with tinge of Napthalene Yellow, Plate 16. Inside of petals—between Scarlet, Plate 1, and Scarlet Red, Plate 1, with White, Plate 53, base. Reverse of petals—Rose Doree, Plate 1, overcast with Scarlet, Plate 1. General tonality from a distance—between Scarlet Red, Plate 1, and Scarlet, Plate 1.

*Discoloration.*—General tonality at end of first day—between Scarlet Red, Plate 1, and Scarlet, Plate 1. Second day—between Scarlet Red, Plate 1, and Scarlet, Plate 1. Third day—between Rose Doree, Plate 1, and Scarlet, Plate 1.

Petals:

*Texture.*—Thin; is not affected by wet or hot weather.

*Appearance.*—Inside—velvety; outside—satiny.

*Form.*—Heart shape.

*Arrangement.*—Imbricated (regularly arranged shinglelike). Petaloids in center—few; small.

*Persistence.*—Drop off cleanly.

*Fragrance.*—Slight. Nature—fruity (Russet apple).

*Lasting quality.*—On the plant and as cut flower—long.

Genital organs:

*Stamens, anthers.*—Small; many. Color—Primuline Yellow, Plate 16. Arrangement—regular around styles.

*Stamens, filaments (threads).*—Short. Color—Amber Yellow, Plate 16.

*Pollen.*—Straw Yellow, Plate 16.

*Styles.*—Bunched, uneven length; short; thin.

*Stigmas.*—Pale Greenish Yellow, Plate 5.

*Ovaries.*—All enclosed in calyx.

*Plant*

Form: Climber.

Growth: Vigorous; upright.

Foliage: 5–7 leaflets.

*Size.*—Medium.

*Quantity.*—Abundant.

*Color.*—New foliage: upper side—Cosse Green, Plate 5; under side—Absinthe

Green, Plate 31. Old foliage: upper side—Dark Cress Green, Plate 31; under side—Light Cress Green, Plate 31.

*Shape.*—Oval pointed.

*Texture.*—Upper side—glossy; under side—smooth. Ribs and veins—prominent.

*Edge.*—Serrated (saw toothed).

*Serration.*—Single; small.

*Rachis.*—Absinthe Green, Plate 31. Under side—rough.

*Stipules.*—Medium length; bearded.

*Disease resistance.*—Resistant.

Wood:

*New wood.*—Color—Lumiere Green, Plate 17. Bark—smooth.

*Old wood.*—Color—Biscay Green, Plate 17. Bark—smooth.

Thorns (thorns are divided into thorns, prickles, and short needles):

*Thorns.*—Quantity—on main stalks from base—few; on laterals from stalk—none. Form—narrow base; short; hooked downward. Color when young—Chamois, Plate 30. Position—irregular.

*Prickles.*—Quantity—on main stalks and on laterals—none.

*Short needles.*—Quantity—on main stalks and on laterals—none.

I claim:

A new and distinct variety of rose plant of the climbing polyantha type, characterized as to novelty by its climbing habit to unusual height for roses of its class, its suitability for pot forcing, its hardiness, the scarlet red color tone of its flowers, persistency of said coloring, and the absence therefrom of blue and purple shadings, substantially as shown and described.

GERRIT DE RUITER.